US008897891B2

(12) United States Patent
Romero

(10) Patent No.: US 8,897,891 B2
(45) Date of Patent: Nov. 25, 2014

(54) LEADS WITH ELECTRODE CARRIER FOR SEGMENTED ELECTRODES AND METHODS OF MAKING AND USING

(71) Applicant: Boston Scientific Neuromodulation Corporation, Valencia, CA (US)

(72) Inventor: Daniel James Romero, Newhall, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/951,057

(22) Filed: Jul. 25, 2013

(65) Prior Publication Data

US 2014/0039587 A1 Feb. 6, 2014

Related U.S. Application Data

(60) Provisional application No. 61/679,264, filed on Aug. 3, 2012.

(51) Int. Cl.
*A61N 1/05* (2006.01)
(52) U.S. Cl.
CPC ............ *A61N 1/0556* (2013.01); *A61N 1/0551* (2013.01)
USPC ........................................................ 607/116
(58) Field of Classification Search
CPC ..... A61N 1/0534; A61N 1/0551; A61N 1/05; A61N 1/0529; A61N 1/0531; A61N 1/0553; A61N 1/0556
USPC .................................................. 607/115–122
See application file for complete search history.

(56) References Cited

U.S. PATENT DOCUMENTS

| 4,602,624 A | 7/1986 | Naples et al. |
| 4,630,611 A | 12/1986 | King |
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |

(Continued)

FOREIGN PATENT DOCUMENTS

| EP | 0580928 A1 | 2/1994 |
| EP | 0650694 B1 | 7/1998 |

(Continued)

OTHER PUBLICATIONS

U.S. Appl. No. 14/053,112, filed Oct. 14, 2013.

(Continued)

*Primary Examiner* — Rex R Holmes
(74) *Attorney, Agent, or Firm* — Lowe Graham Jones PLLC; Bruce E. Black

(57) ABSTRACT

A stimulation lead includes a lead body having a longitudinal length, a distal portion, and a proximal portion; terminals disposed along the proximal portion of the lead body; an electrode carrier coupled to, or disposed along, the distal portion of the lead body; segmented electrodes disposed along the electrode carrier; and conductors extending along the lead body and coupling the segmented electrodes to the terminals. The electrode carrier includes a lattice region defining segmented electrode receiving openings. Each of the segmented electrodes extends around no more than 75% of a circumference of the lead and is disposed in a different one of the segmented electrode receiving openings of the electrode carrier.

20 Claims, 5 Drawing Sheets

(56) References Cited

U.S. PATENT DOCUMENTS

| | | |
|---|---|---|
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,181,969 B1 | 1/2001 | Gord |
| 6,322,559 B1 | 11/2001 | Daulton et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,244,150 B1 | 7/2007 | Brase et al. |
| 7,292,890 B2 | 11/2007 | Whitehurst et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,809,446 B2 | 10/2010 | Meadows |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,175,710 B2 | 5/2012 | He |
| 8,224,450 B2 | 7/2012 | Brase |
| 8,225,504 B2 | 7/2012 | Dye et al. |
| 8,271,094 B1 | 9/2012 | Moffitt et al. |
| 8,295,944 B2 | 10/2012 | Howard et al. |
| 8,321,025 B2 | 11/2012 | Bedenbaugh |
| 8,364,278 B2 | 1/2013 | Pianca et al. |
| 8,391,985 B2 | 3/2013 | McDonald |
| 8,583,237 B2 | 11/2013 | Bedenbaugh |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0173262 A1* | 8/2006 | Hegland et al. ............... 600/373 |
| 2006/0247697 A1 | 11/2006 | Sharma et al. |
| 2007/0150036 A1 | 6/2007 | Anderson |
| 2007/0203546 A1 | 8/2007 | Stone et al. |
| 2008/0103580 A1 | 5/2008 | Gerber |
| 2008/0114230 A1 | 5/2008 | Addis |
| 2008/0215125 A1 | 9/2008 | Farah et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009025816 A1 | 2/2009 |
| WO | 2009102536 A1 | 8/2009 |

OTHER PUBLICATIONS

U.S. Appl. No. 13/787,171, filed Mar. 6, 2013.
U.S. Appl. No. 13/899,316, filed May 21, 2013.
U.S. Appl. No. 12/177,823, filed Jul. 22, 2008.
U.S. Appl. No. 13/750,725, filed Jan. 25, 2013.
U.S. Appl. No. 13/906,776, filed May 31, 2013.

* cited by examiner

LEADS WITH ELECTRODE CARRIER FOR SEGMENTED ELECTRODES AND METHODS OF MAKING AND USING

CROSS-REFERENCE TO RELATED APPLICATIONS

This application claims the benefit under 35 U.S.C. §119(e) of U.S. Provisional Patent Application Ser. No. 61/679,264 filed on Aug. 3, 2012, which is incorporated herein by reference.

FIELD

The invention is directed to the area of electrical stimulation systems and methods of making and using the systems. The present invention is also directed to electrical stimulation leads with segmented electrodes that can be used for directed electrical stimulation, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a stimulation lead that includes a lead body having a longitudinal length, a distal portion, and a proximal portion; terminals disposed along the proximal portion of the lead body; an electrode carrier coupled to, or disposed along, the distal portion of the lead body; segmented electrodes disposed along the electrode carrier; and conductors extending along the lead body and coupling the segmented electrodes to the terminals. The electrode carrier includes a lattice region defining segmented electrode receiving openings. Each of the segmented electrodes extends around no more than 75% of a circumference of the lead and is disposed in a different one of the segmented electrode receiving openings of the electrode carrier. Optionally, the stimulation lead can include one or more ring electrodes disposed on the electrode carrier and coupled via one or more conductors to the terminals.

Another embodiment is a method of making a stimulation lead. The method includes providing an electrode carrier having a lattice region defining multiple segmented electrodes receiving openings; and disposing segmented electrodes in the segmented electrode receiving openings. Each of the segmented electrodes extends around no more than 75% of a circumference of the lead and each of the segmented electrodes is disposed in a different one of the segmented electrode receiving openings of the electrode carrier. The method also includes electrically coupling conductors to the segmented electrodes and electrically coupling the conductors to terminals disposed along an opposing end of the lead. Optionally, the method can include disposing one or more ring electrodes on the electrode carrier and electrically coupling the one or more ring electrodes to the terminals via one or more conductors.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems. The present invention is also directed to electrical stimulation leads with segmented electrodes that can be used for directed electrical stimulation, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

Figure 1:
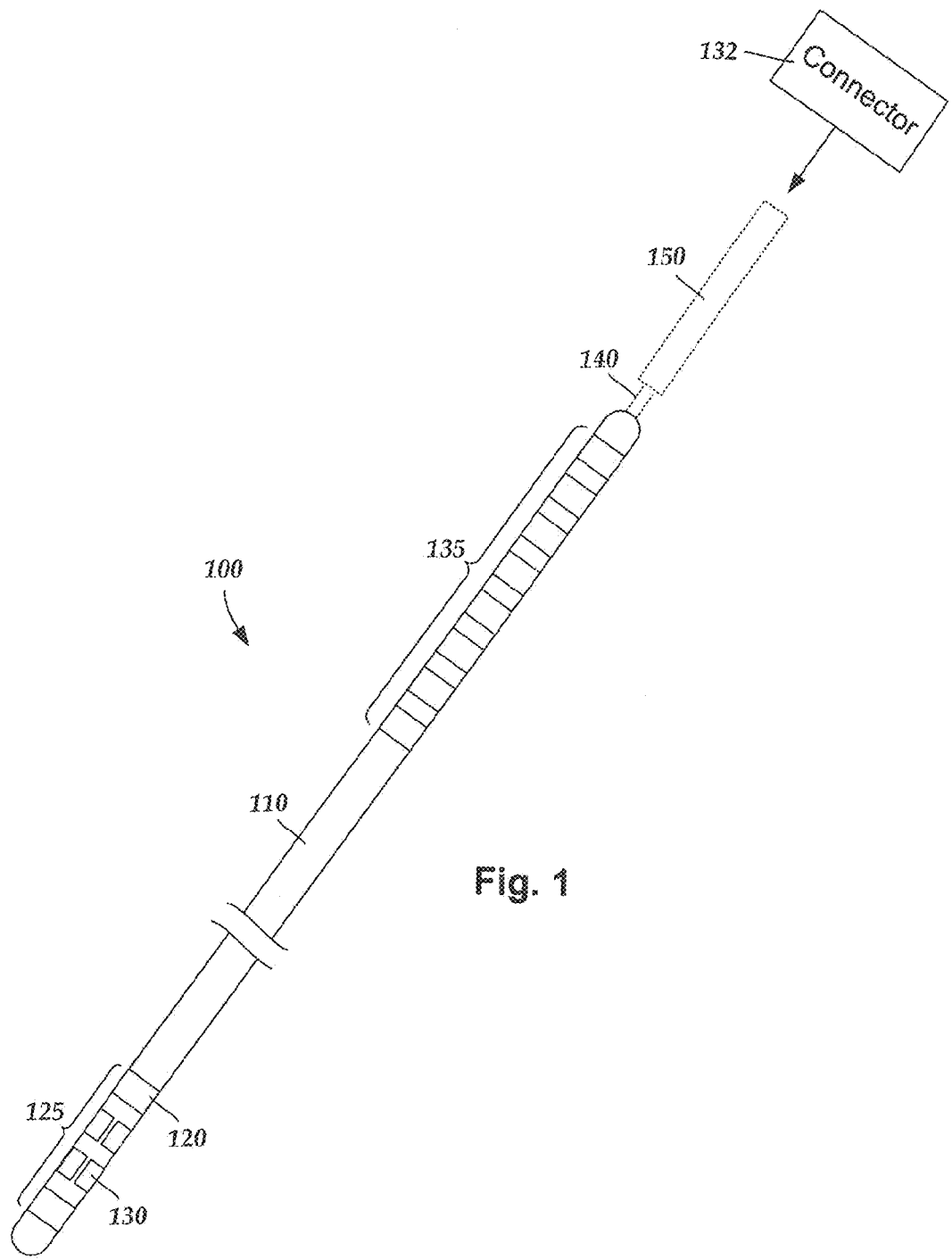
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more or fewer than eight stimulation channels (e.g., 4-, 6-, 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 1 to 1.5 mm.

In at least some embodiments, the lead 100 has a length of at least 10 cm and the length of the lead 100 may be in the range of 25 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 may be disposed on any part of the lead body 110, usually near a distal end of the lead 100. In FIG. 1, the lead 100 includes two ring electrodes 120. Any number of ring electrodes 120 may be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes may be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,295,944; and 8,391,985; and U.S. Patent Applications Publication Nos. 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated herein by reference.

In FIG. 1, the lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

Figure 3:
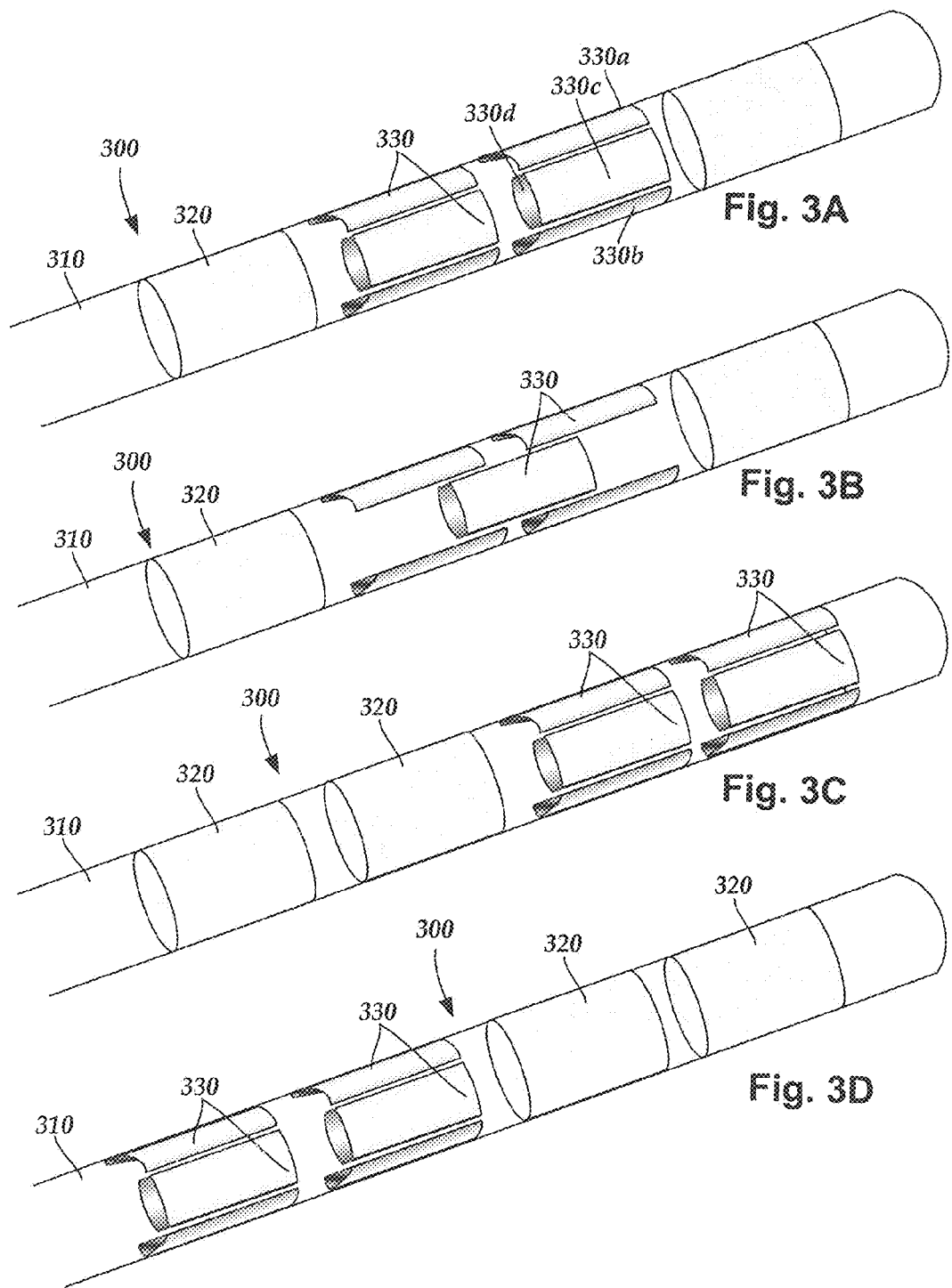
FIG. 3A is a perspective view of an embodiment of a portion of a lead having a plurality of segmented electrodes, according to the invention.
FIG. 3B is a perspective view of a second embodiment of a portion of a lead having a plurality of segmented electrodes, according to the invention.
FIG. 3C is a perspective view of a third embodiment of a portion of a lead having a plurality of segmented electrodes, according to the invention.
FIG. 3D is a perspective view of a fourth embodiment of a portion of a lead having a plurality of segmented electrodes, according to the invention.

When the lead 100 includes both ring electrodes 120 and segmented electrodes 130, the ring electrodes 120 and the segmented electrodes 130 may be arranged in any suitable configuration. For example, when the lead 100 includes two sets of ring electrodes 120 and two sets of segmented electrodes 130, the ring electrodes 120 can flank the two sets of segmented electrodes 130 (see e.g., FIG. 1). Alternately, the two sets of ring electrodes 120 can be disposed proximal to the two sets of segmented electrodes 130 (see e.g., FIG. 3C), or the two sets of ring electrodes 120 can be disposed distal to the two sets of segmented electrodes 130 (see e.g., FIG. 3D). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration. It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
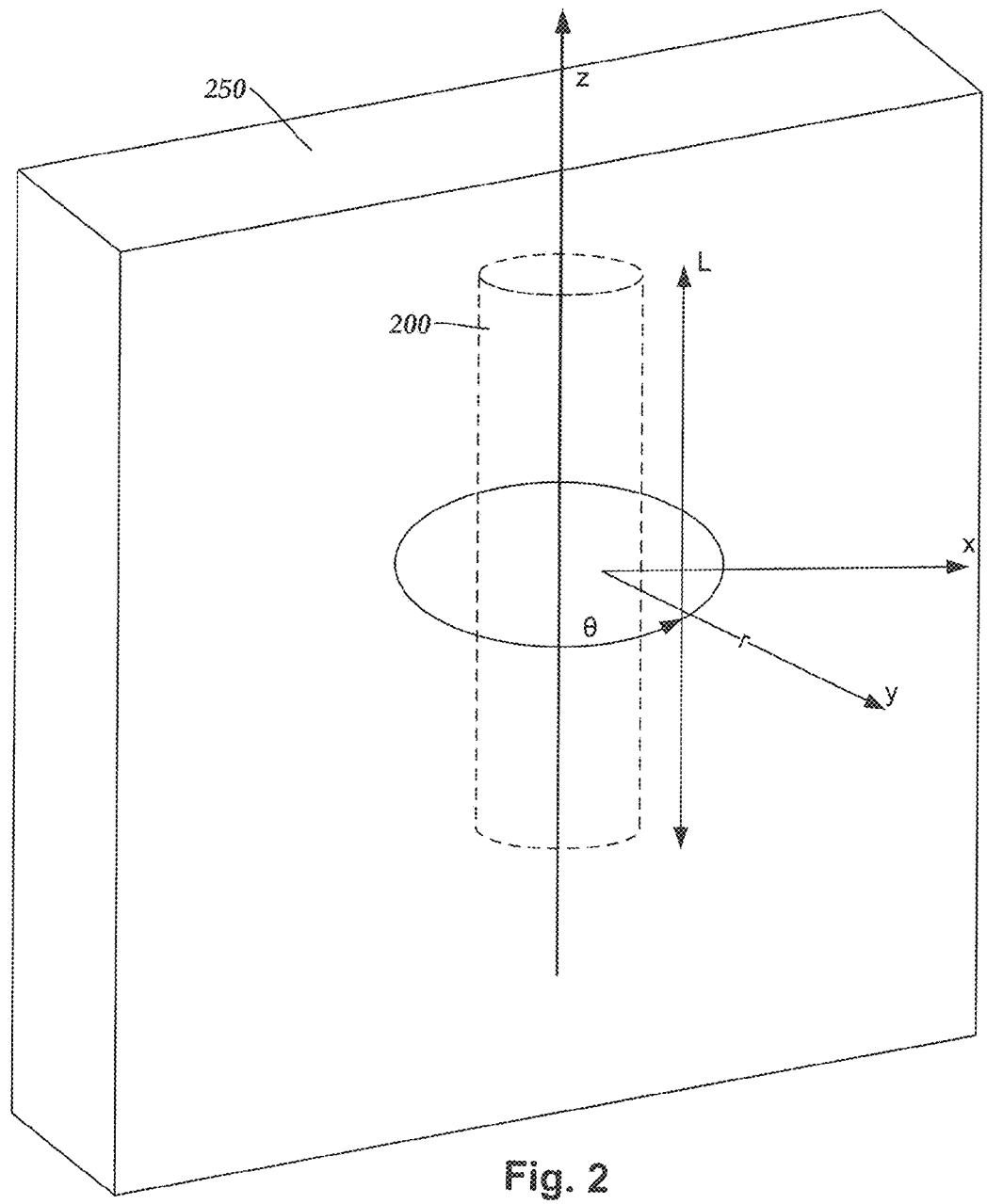
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

In other embodiments, individual electrodes in the two sets of segmented electrodes 130 are staggered (see, FIG. 3B) relative to one another along the length of the lead body 110. In some cases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

FIGS. 3A-3D illustrate leads 300 with segmented electrodes 330, optional ring electrodes 320, and a lead body 310. The sets of segmented electrodes 330 include either two (FIG. 3B) or four (FIGS. 3A, 3C, and 3D) or any other number of segmented electrodes including, for example, three, five, six, or more.

Any other suitable arrangements of segmented electrodes can be used. As an example, arrangements in which segmented electrodes are arranged helically with respect to each other. One embodiment includes a double helix.

One challenge to making leads with segmented electrodes is the correct placement of the electrodes, and retention of the desired electrode placement, during the manufacturing process. An electrode carrier can be utilized to hold the electrodes in the desired spatial arrangement during the manufacture of the lead. The electrode carrier is made of a non-conductive material to electrically isolate the segmented electrodes from each other and from the ring electrodes, if present.

Figure 4:
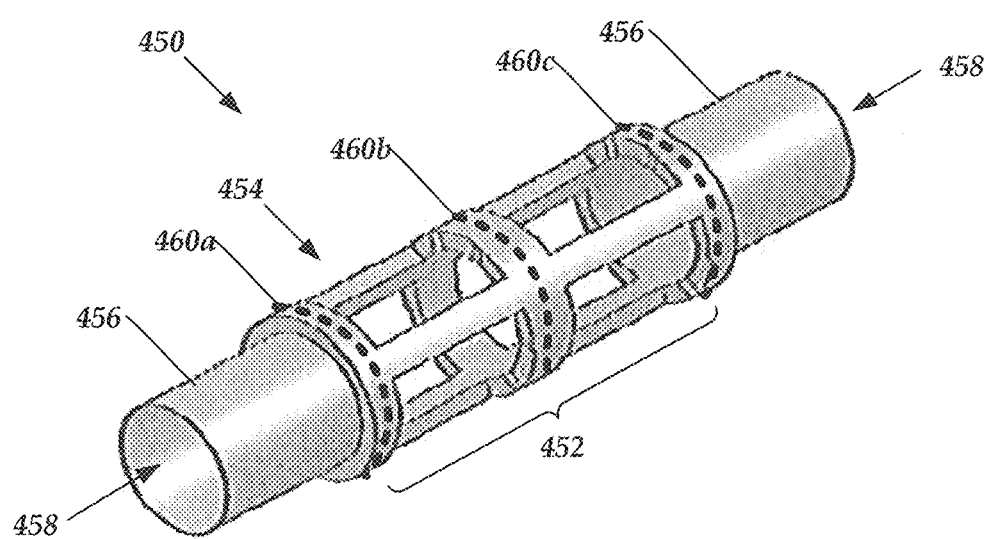
FIG. 4 is a schematic perspective view of one embodiment of an electrode carrier, according to the invention.

FIG. 4 illustrates one embodiment of an electrode carrier 450. The electrode carrier 450 includes a lattice region 452 that defines segmented electrode receiving openings 454 where the segmented electrodes are to be placed (see, for example, FIG. 5). In the illustrated example, lattice region 452 of the electrode carrier 450 is designed for two sets of segmented electrodes with each set having three segmented electrodes. It will be recognized that other electrode carriers can be designed that include a different number of sets of segmented electrodes, a different number of segmented electrodes in a set, or a different spatial arrangement of the segmented electrodes (e.g., with sets staggered with respect to each other or with some or all of the segmented electrodes not arranged in sets), or any combination thereof.

Figure 5A:
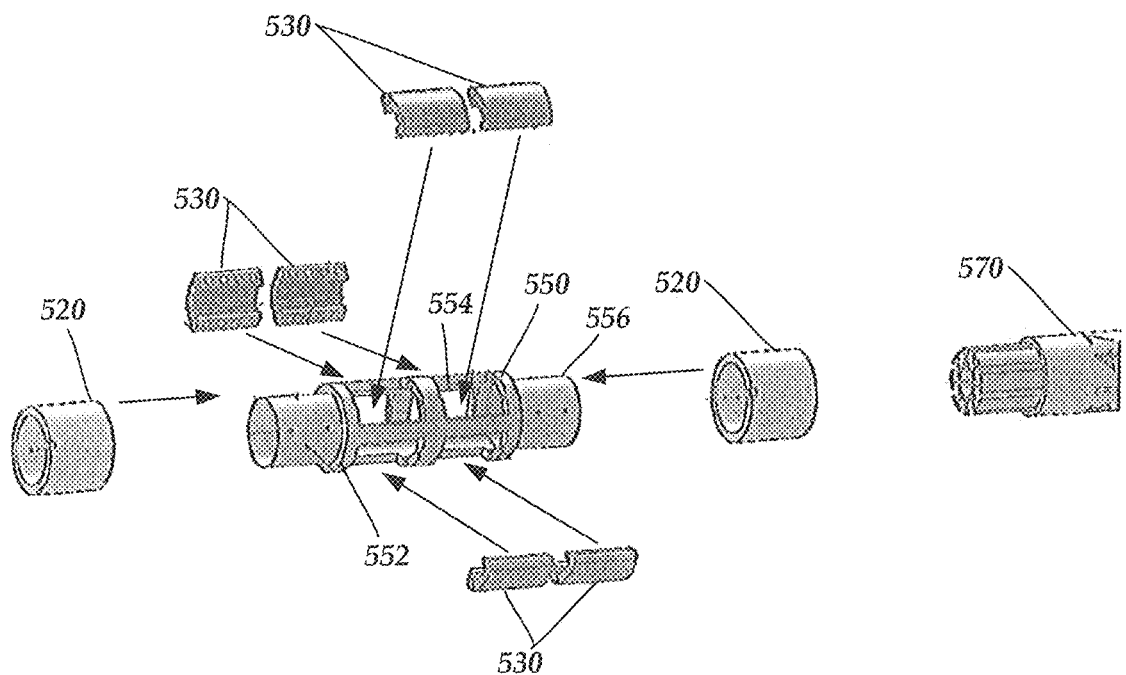
FIG. 5A is a schematic exploded perspective view of one embodiment of a portion of lead illustrating an electrode carrier and associated segmented and ring electrodes, according to the invention.

The electrode carrier 450 may also include one or more tubular features 456 to receive a ring electrode (see, for example, FIG. 5A). The tubular features 456 may be provided on the proximal or distal ends (or both ends as illustrated in FIG. 4) of the electrode carrier 450. Alternatively or additionally, one or more tubular features can be provided at other locations on the electrode carrier if the ring electrode can be disposed around the tubular feature (for example, if the electrode has a "C" shape, or is a flexible strip, and can be wrapped, snapped, crimped, adhered, or otherwise disposed or fastened around the tubular feature.) In some embodiments, the distal-most ring electrode may be a tip electrode which has a closed end. Examples of a tip electrode can be found at, for example, U.S. patent application Ser. No. 13/906,776, incorporated herein by reference.

The electrode carrier 450 may also have a central lumen 458 through which conductors (see, FIG. 5B) attached to the segmented electrodes or ring electrodes can pass on the way to the remainder of the lead. The central lumen 458 may be open at both ends of the electrode carrier 450 or may be closed at the distal end of the electrode carrier.

The electrode carrier 450, or at least the lattice region 452, is formed of a non-conductive material which may be the same material as the lead body, for example, silicone, polyurethane, polyetheretherketone, or any other suitable biocompatible material. In some embodiments, the electrode carrier 450 may be made of a material that is stiffer or harder than the material of the lead body. For example, the material of the electrode carrier 450 may have a higher durometer than that of the lead body. In some embodiments, the electrode carrier 450 is made of the same type of polymer material (e.g., polyurethane or silicone) as the lead body, but with a higher durometer than the lead body. A stiffer or harder material for the electrode carrier may facilitate manufacturing.

Optionally, the electrode carrier 450 may be designed to allow a user to break the electrode carrier at predefined positions, such as one or more of breakage positions 460a, 460b, 460c. It will be understood that any of these positions, alone or in combination, may be selected for a breakage position or one or more other positions may be selected. The electrode carrier at the one or more breakage positions may be weakened. For example, the electrode carrier may have perforations, indentations, grooves, striations, or other arrangements that allow a user to break the carrier at the predefined positions. In at least some embodiments, breakage at these positions may occur, for example, after formation of the lead body or just prior to implantation. It will be understood that even if the breakage position is present in the electrode carrier, breakage of the electrode carrier does not necessarily occur. The breakage of the carrier at one or more breakage positions may reduce the stiffness of the lead at the distal end where the carrier resides. The stiffness of the carrier may be desirable during manufacture, but less desirable when the lead is implanted.

FIG. 5A is an exploded view of an electrode carrier 550, segmented electrodes 530, ring electrodes 520, and a portion of the lead 570. The arrows in FIG. 5A indicate the places that the electrodes 520, 530 are attached onto the electrode carrier 550.

The segmented electrodes 530 fit into the segmented electrode receiving openings 554 of the lattice portion 552 of the electrode carrier 550. In some embodiments, the segmented electrodes 530 may form a friction fit with, or snap into, the lattice portion 552 surrounding the respective segmented electrode receiving openings 554. In other embodiments, the segmented electrodes 530 may be held within the openings 554 merely by applying tension to conductors (see FIG. 5B) attached to the segmented electrodes. In some embodiments, adhesive or other fastening mechanisms may be used to hold the segmented electrodes in place once positioned.

The ring electrodes 530 fit onto the tubular features 556 of the electrode carrier 550. In some embodiments, the ring electrodes 520 may form a friction fit with, or snap onto, the tubular features 556. In other embodiments, the ring electrodes 520 may be held on the tubular features 556 merely by applying tension to conductors (see FIG. 5B) attached to the ring electrodes. In some embodiments, adhesive or other fastening mechanisms may be used to hold the ring electrodes in place once positioned.

In some embodiments, the other surface of the segmented electrodes 530 and the outer surface of the lattice portion 552 of the electrode carrier 550 may form an isodiametric arrangement when the segmented electrodes are nested in the segmented electrode receiving openings 554. Optionally, the outer surface of the lattice portion 552 may also be isodiametric with the outer surface of the ring electrodes 520 when the ring electrodes 520 are seated on the tubular features 556 of the electrode carrier 550.

In other embodiments, the outer surface of the lattice portion 552 may be recessed with respect to the outer surface of the segmented electrodes 552 when the segmented electrodes are nested in the segmented electrode receiving openings 554. Optionally, the outer surface of the lattice portion 552 may also be recessed with respect to the outer surface of the ring electrodes 520 when the ring electrodes 520 are seated on the tubular features 556 of the electrode carrier 550. Such arrangements may facilitate the formation of a portion of the lead body (for example, a jacket) between the segmented electrodes (and optionally between the ring electrodes and adjacent segmented electrodes) and over the lattice portion of the electrode carrier.

In some embodiments, the longitudinal length of one or more of the tubular features 556 is equal to the longitudinal length of the ring electrode 520 positioned thereon. In some embodiments, the longitudinal length of one or more of the tubular features 556 is less than the longitudinal length of the ring electrode 520 positioned thereon. This may facilitate attachment to a portion of the lead 570 to the electrode carrier and electrodes using the proximal-most ring electrode for attachment or may facilitate attachment of an end cap (not shown) using the distal-most ring electrode for attachment. In some embodiments, the longitudinal length of one or more of the tubular features 556 is greater than the longitudinal length of the ring electrode 520 positioned thereon. This may facilitate attachment to a portion of the lead 570 to the electrode carrier and electrodes using the proximal-most tubular feature for attachment or may facilitate attachment of an end cap (see, FIG. 1 for lead with end cap distal to ring electrode) using the distal-most tubular feature for attachment.

Figure 5B:
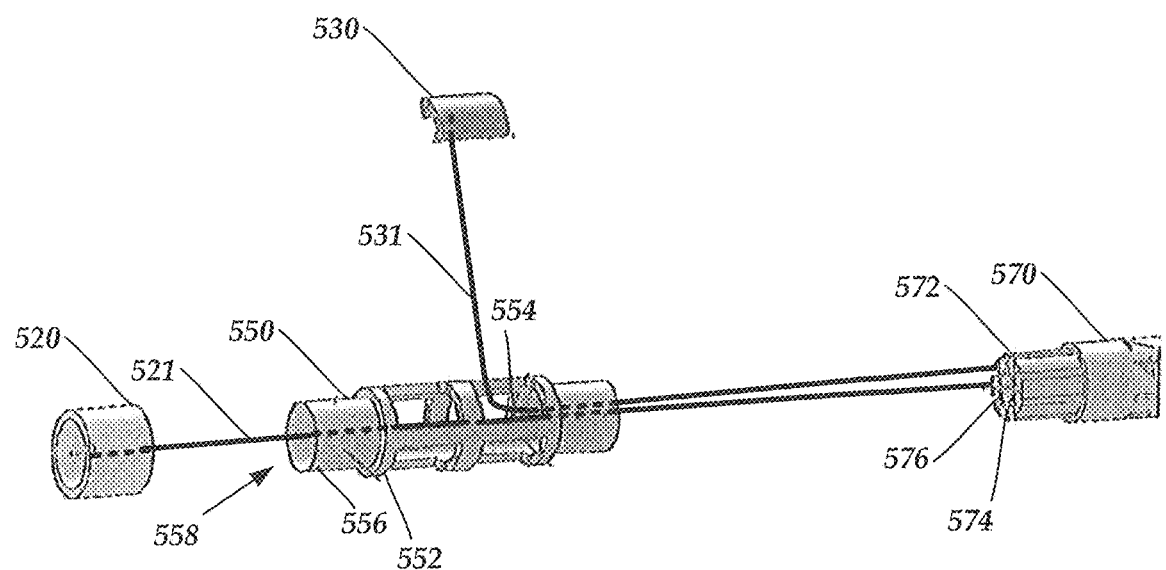
FIG. 5B is a schematic exploded perspective view of one embodiment of a portion of lead illustrating an electrode carrier and selected segmented and ring electrodes with associated conductors, according to the invention.

FIG. 5B illustrates one embodiment of a ring electrode 520 and a segmented electrode 530 each electrically coupled to a respective conductor 521, 531. The conductors 521, 531 can be attached to the respective electrodes 520, 530 using any suitable method including, but not limited to, welding, soldering, adhesively attaching, or the like. Only these two electrodes are illustrated for clarity, but it will be understood that each of the other electrodes (see FIG. 5A) can be similarly attached to a conductor.

The conductor 521 is threaded through the central lumen 558 of the electrode carrier 550 to the portion of the lead 570. The conductor 531 is threaded through the segmented electrode receiving opening 554 that is to receive the segmented electrode 530. The conductor 531 proceeds through the central lumen 558 to the portion of the lead 570. In some embodiments, the electrodes 520, 530 may be held on the electrode carrier 550 by applying tension to the conductors 521, 531 attached to the electrodes. It will be understood that the conductors 521, 531 can be attached to the electrodes 520, 530 prior to or after threading the conductors through the electrode carrier 550. It will also be understood that the conductors 521, 531 can be attached to the electrodes 520, 530 prior to or after threading the conductors into the portion of the lead 570.

The lead 570 may include a conductor tube 572 that carries the conductors through the lead to its proximal end. In the illustrated embodiment, the conductor tube 572 includes peripheral lumens 574 surrounding a central lumen 576. Each of the peripheral lumens can carry one or more conductors and the central lumen can carry one or more conductors or may be useful as a stylet lumen. In some embodiments, each conductor 521, 531 is threaded through a different one of the peripheral lumens.

Figure 5C:
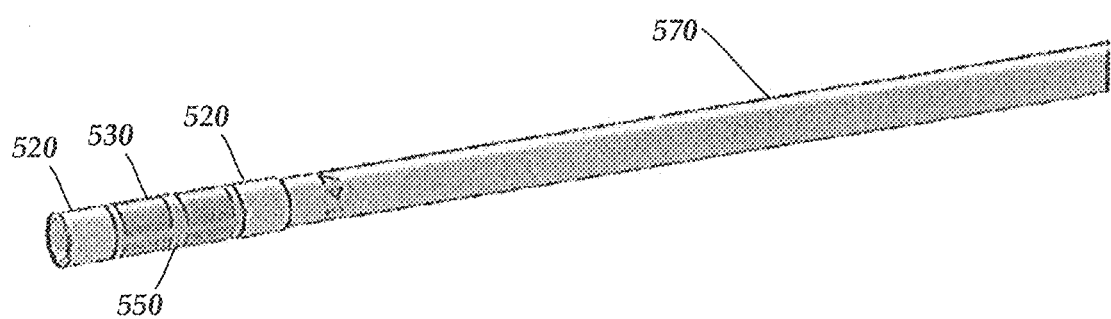
FIG. 5C is a schematic perspective view of one embodiment of a portion of a lead showing the electrode carrier with electrodes attached to a remainder of the lead, according to the invention.

FIG. 5C illustrated one embodiment of a lead 570 with the electrode carrier 550 disposed on the lead and the electrodes 520, 530 seated in the electrode carrier. In some embodiments, the electrode carrier 550 may form part of the exterior surface of the lead body. In other embodiments, a lead body may be formed over the electrode carrier (see, FIG. 1).

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulation lead, comprising:
    a lead body comprising a longitudinal length, a distal portion, and a proximal portion;
    a plurality of terminals disposed along the proximal portion of the lead body;
    a single electrode carrier coupled to, or disposed along, the distal portion of the lead body, the electrode carrier comprising a lattice region defining a plurality of segmented electrode receiving openings, wherein the lattice region is formed of a non-conductive material; wherein the segmented electrode recieving openings are arranged in a plurality of sets with each of the sets being disposed at a different longitudinal position along the lead;
    a plurality of electrodes comprising a plurality of segmented electrodes, each of the segmented electrodes extending around no more than 75% of a circumference of the lead, each of the segmented electrodes disposed in a different one of the segmented electrode receiving openings of the electrode carrier; and wherein a proximal portion of the electrode carrier is disposed proximal to all of the segmented electrodes and a portion of the lead body is disposed over the proximal portion of the electrode carrier; and
    a plurality of conductors extending along the lead body and coupling the plurality of electrodes to the plurality of terminals.

2. The stimulation lead of claim 1, wherein the plurality of electrodes comprises a plurality of sets of the segmented electrodes, each set of the segmented electrodes comprising a plurality of the segmented electrodes disposed at a same longitudinal position along the lead.

3. The stimulation lead of claim 1, wherein the plurality of electrodes further comprises at least one ring electrode.

4. The stimulation lead of claim 3, wherein the at least one ring electrode is disposed on the electrode carrier.

5. The stimulation lead of claim 4, wherein the electrode carrier comprises at least one tubular structure upon which at least one of the at least ring electrode is disposed.

6. The stimulation lead of claim 5, wherein at least one of the at least one tubular structure is disposed on a distal end of the electrode carrier.

7. The stimulation lead of claim 5, wherein at least one of the at least one tubular structure is disposed on a proximal end of the electrode carrier.

8. The stimulation lead of claim 1, wherein the electrode carrier further comprises at least one breakage position configured and arranged to be weakened relative to adjacent portions of the electrode carrier to permit breakage of the electrode carrier after manufacture of the stimulation lead.

9. The stimulation lead of claim 8, wherein the plurality of segmented electrode receiving openings comprises a plurality of sets of the segmented electrode receiving openings, each set of the segmented electrode receiving openings comprising a plurality of the segmented electrode receiving openings disposed at a same longitudinal position along the electrode carrier, wherein the at least one breakage position comprises a first breakage position disposed between two sets of the segmented electrode receiving openings.

10. The stimulation lead of claim 8, wherein the electrode carrier comprises at least one tubular structure and the at least one breakage position comprises a second breakage position disposed between the lattice region and a one of the at least one tubular structure.

11. The stimulation lead of claim 1, wherein the electrode carrier defines a central lumen through which at least a portion of the plurality of conductors passes.

12. The stimulation lead of claim 1, wherein the electrode carrier is formed of the non-conductive material.

13. The stimulation lead of claim 1, wherein the lead body is formed of a different material from the electrode carrier.

14. A method of making the stimulation lead of claim 1, the method comprising:
    providing an electrode carrier comprising a lattice region defining a plurality of segmented electrode receiving openings, wherein the lattice region is formed of a non-conductive material;
    disposing a plurality of segmented electrodes in the plurality of segmented electrode receiving openings, each of the segmented electrodes extending around no more than 75% of a circumference of the lead, each of the segmented electrodes disposed in a different one of the segmented electrode receiving openings of the electrode carrier; and
    electrically coupling a plurality of conductors to the plurality of segmented electrodes and electrically coupling the plurality of conductors to a plurality of terminals disposed along an opposing end of the lead.

15. The method of claim 14, wherein electrically coupling the plurality of conductors to the plurality of segmented electrodes occurs prior to disposing the plurality of segmented electrodes in the plurality of segmented electrode receiving openings.

16. The method of claim 14, further comprising threading the plurality of conductors through the plurality of segmented electrode receiving openings and into a central lumen of the electrode carrier.

17. The method of claim 14, wherein the electrode carrier further comprises at least one tubular structure and the method further comprises disposing at least one ring electrode on the at least one tubular structure of the electrode carrier.

18. The method of claim 17, further comprising electrically coupling at least one second conductor to the at least one ring electrode and threading the at least one second conductors through the at least one tubular structure and into a central lumen of the electrode carrier.

19. The method of claim 14, further comprising forming a portion of a lead body over a portion the electrode carrier.

20. The method of claim 14, further comprising breaking the electrode carrier at at least one breakage point after disposing the plurality of segmented electrodes in the plurality of segmented electrode receiving openings.

\* \* \* \* \*